United States Patent [19]

Krause et al.

[11] 4,402,849
[45] Sep. 6, 1983

[54] LIQUID-CRYSTALLINE TETRAHYDROQUINAZOLINES

[75] Inventors: Joachim Krause, Dieburg; Ludwig Pohl, Darmstadt, both of Fed. Rep. of Germany

[73] Assignee: Merck Patent Gesellschaft mit beschränkter Haftung, Darmstadt, Fed. Rep. of Germany

[21] Appl. No.: 218,239

[22] Filed: Dec. 19, 1980

[30] Foreign Application Priority Data

Dec. 19, 1979 [DE]  Fed. Rep. of Germany ....... 2951099

[51] Int. Cl.³ ............................ C09K 3/34; G02F 1/13; C07D 239/74
[52] U.S. Cl. ............................ 252/299.61; 350/350 R; 544/283; 252/299.62
[58] Field of Search ............... 544/283; 260/299.61; 350/350 R

[56] References Cited

U.S. PATENT DOCUMENTS

| | | | |
|---|---|---|---|
| 3,574,210 | 4/1971 | Breuer et al. | 544/283 |
| 3,637,693 | 1/1972 | Otterstedt et al. | 544/283 |
| 3,997,536 | 12/1976 | Boller et al. | 260/465 E |
| 4,062,798 | 12/1977 | Boller et al. | 260/465 E |
| 4,181,625 | 1/1980 | Eidenschink et al. | 350/350 |
| 4,273,929 | 6/1981 | Boller et al. | 544/242 |

FOREIGN PATENT DOCUMENTS

| | | | |
|---|---|---|---|
| 25598 | 3/1981 | European Pat. Off. | 252/299.62 |
| 2949080 | 6/1981 | Fed. Rep. of Germany | 252/299.62 |
| 2090593 | 7/1982 | United Kingdom | 252/299.62 |

*Primary Examiner*—Donald G. Daus
*Assistant Examiner*—James H. Turnipseed
*Attorney, Agent, or Firm*—Millen & White

[57] ABSTRACT

Liquid-crystalline tetrahydroquinazolines of the formula

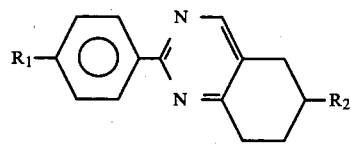

wherein $R_1$ is alkyl, alkoxy, alkanoyloxy or alkoxycarbonyloxy of up to 8 carbon atoms in each case, CN, $CF_3$, halogen or $NO_2$; and $R_2$ is alkyl of up to 10 carbon atoms are valuable components for liquid crystalline dielectrics.

7 Claims, No Drawings

LIQUID-CRYSTALLINE TETRAHYDROQUINAZOLINES

BACKGROUND OF THE INVENTION

The properties of nematic or nematic-cholesteric liquid-crystalline materials are increasingly utilized for electro-optical display elements in order to effect significant changes in the optical properties of the latter, such as light absorption, light scattering, birefringence, reflectance or color, under the influence of electric fields. The functioning of display elements of this type is based, for example, on the phenomena of dynamic scattering, the deformation of aligned phases, the Schadt-Helfrich effect in the twisted cell or the cholesteric-nematic phase transition.

For the technical application of these effects to electronic components, liquid-crystalline dielectrics are required which must fulfill a large number of requirements. Chemical resistance to moisture, air and physical influences, such as heat, radiation in the infrared, visible and ultraviolet ranges and continuous and alternating electric fields, is of particular importance. Industrially usable liquid-crystalline dielectrics are also required to have a liquid-crystalline mesophase in the temperature range from at least $+10°$ C. to $+50°$ C., preferably from $0°$ C. to $60°$ C., and the lowest possible viscosity at room temperature, which preferably should not exceed $70 \times 10^{-3}$ Pa.s. Finally, they must not have any characteristic absorption in the range of visible light, i.e., they must be colorless.

A number of liquid-crystalline compounds has already been disclosed, which fulfill the stability demands made for dielectrics intended for electronic components, and which are also colorless. These include, in particular, the p,p'-disubstituted phenyl benzoates described in German Offenlegungsschrift No. 2,139,628 and the p,p'disubstituted phenylcyclohexane derivatives described in German Offenlegungsschrift No. 2,636,684. In the two classes of compounds mentioned, and also in other known series of compounds with a liquid-crystalline mesophase, there are no individual compounds which form a liquid-crystalline nematic mesophase in the required temperature range from $10°$ C. to $60°$ C. As a rule, mixtures of two or more compounds are therefore prepared, in order to obtain substances which can be used as liquid-crystalline dielectrics. For this purpose, a compound having a low melting point and clear point is usually mixed with another compound having a markedly higher melting point and clear point. This normally gives a mixture, the melting point of which is below that of the lower melting component, while the clear point is between the clear points of the components. It is, however, not easy to prepare optimum dielectrics in this way, since the components having the high melting points and clear points frequently also impart a high viscosity to the mixtures. As a result, the switching times of the electro-optical display elements, produced with these mixtures, are extended in an undesirable manner.

SUMMARY OF THE INVENTION

Accordingly, it is an object of this invention to prepare liquid-crystalline dielectrics which have a nematic phase within the required temperature range and, enable switching times in liquid crystal cells, which are sufficiently short at room temperatures.

Upon further study of the specification and appended claims, further objects and advantages of this invention will become apparent to those skilled in the art.

These objects have been achieved by this invention by providing tetrahydroquinazolines of formula (I)

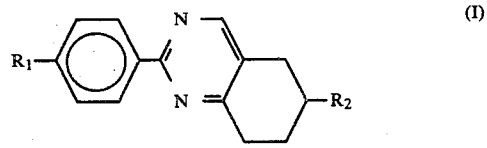

wherein $R_1$ is alkyl, alkoxy, alkanoyloxy or alkoxycarbonyloxy of up to 8 carbon atoms in each case, CN, $CF_3$, halogen or $NO_2$ and $R_2$ is alkyl of up to 10 carbon atoms. These are outstandingly suitable as components of liquid-crystalline dielectrics. They are particularly useful for widening the temperature range of the nematic phase, because they have high clear points in conjunction with melting points which are surprisingly low for this type of structure. Moreover, the compounds of formula (I) have a positive dielectric anisotropy (DCA) which is more or less pronounced, depending on the nature of the wing groups $R_1$ and $R_2$.

The compounds of formula (I) are therefore used above all for modifying the DCA of liquid-crystalline dielectrics. In particular, those compounds in which $R_1$ is a polar group, such as CN, $CF_3$, halogen or $NO_2$, have an astonishingly high positive DCA and are therefore preferentially employed in those dielectrics which are used for electro-optical display elements based on the principle of the twisted nematic cell (TNC) or the cholesteric-nematic phase transition. In display elements of this type, they make it possible to render information visible, with very low threshold voltages or operating voltages.

In the pure state, the compounds of formula (I) are colorless and chemically and photochemically very stable. Alone, or in combination with other liquid-crystalline substances, they form nematic mesophases having a surprisingly low viscosity.

The present invention thus relates to the tetrahydroquinazolines of formula (I), to their manufacture and to their use as components of liquid-crystalline dielectrics. Furthermore, the present invention relates to liquid-crystalline dielectrics containing at least one tetrahydroquinazoline of formula (I) and to electro-optical display elements which are based on a liquid crystal cell and contain a liquid-crystalline dielectric of this type.

DETAILED DISCUSSION

In the compounds of this invention, the alkyl groups which represent the wing groups $R_2$ and if appropriate $R_1$, or the alkyl portions of the alkoxy, alkanoyloxy or alkoxycarbonyloxy groups for the wing group $R_1$, can be straight-chain or branched. However, the compounds of this invention may preferably contain at most only one branched alkyl group. Among the compounds of this invention having 2 chain-type wing groups, however, those in which these two wing groups have straight chains are preferred, because the compounds as a rule then have markedly higher clear points.

Compounds of this invention of formula (I), having a branched wing group $R_1$ or $R_2$ are occasionally important because of a higher solubility in the conventional liquid-crystalline base materials, but particularly as chiral doping substances if they possess optical activity due to the chain branching. Such branched substituents do not contain more than one chain branching. Preferred branched radicals are those in which a methyl or ethyl group is located in the 2- or 3-position on a relatively long carbon chain, for example, 2-methylpropyl, 2-methylbutyl, 3-methylbutyl, 2-methylpentyl, 3-methylpentyl, 2-ethylhexyl or 2-methylhexyl.

According to the foregoing, the wing groups of the compounds of this invention together can contain up to 18 carbon atoms. Among these, those compounds are preferred in which the wing groups together contain 2 to 14, in particular 3 to 12, carbon atoms.

When wing group $R_1$ is halogen, $CF_3$, $NO_2$ or preferably CN, the compounds of this invention have a particularly strongly pronounced positive DCA which reaches values of up to $+35$. Compounds from this group are preferentially used for increasing the DCA, for example in place of 4-dimethylaminobenzonitrile which is employed for this purpose according to German Patent Specification No. 2,321,632.

Halogen includes F, Cl and Br.

The compounds of this invention can be prepared in a manner which is conventional for substances of this type, for example, by reacting a 4-alkyl-2-hydroxymethylene-cyclohexanone of the formula (II)

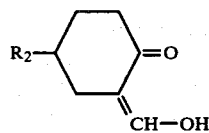

(II)

wherein $R_2$ is alkyl of up to 10 carbon atoms, with a benzamidine hydrochloride of formula (III)

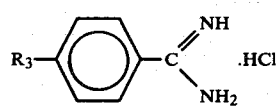

(III)

in the presence of a basic condensation agent. $R_3$ can be any of those groups for $R_1$ of formula (I), which are stable under the conditions of condensation reactions of this type, i.e., in particular, alkyl, alkoxy, halogen or $NO_2$. Moreover, $R_3$ can also represent other groups which are stable under these conditions and which can readily be converted into other radicals $R_1$, particularly the benzyloxy group, for example.

Suitable basic condensation agents for use in the process of this invention include, for example, alkali metal alcoholates or alkali metal hydroxides in alcohols, and also organic bases, such as, for example, piperidine in alcohol or pyridine. Preferably, sodium methylate or sodium ethylate in methanol or ethanol respectively are used. The reaction is generally carried out at a temperature of 20° to 120°, preferably in boiling methanol or ethanol. Under these conditions, the reaction is complete, as a rule, after 1–10 hours. The reaction mixture can be worked up in a manner which is conventional per se, usually by evaporation, take-up in water and extraction of the resulting tetrahydroquinazoline with ether.

The conversion, which may follow, of an undesired radical $R_3$ into a desired radical $R_1$ can be carried out under conditions which are usual for reactions of this type. Thus, for example, 2-(p-benzyloxyphenyl)-tetrahydroquinazolines (formula IV, $R_3$=benzyloxy)

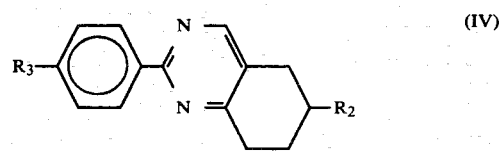

(IV)

can be hydrolytically or hydrogenolytically split to the corresponding 2-(p-hydroxyphenyl)-tetrahydroquinazolines, and are then converted by means of an alkanoyl chloride or alkoxycarbonyl chloride into compounds of formula (I) in which $R_1$ denotes alkanoyloxy or alkoxycarbonyloxy. By reacting a compound of formula (IV) in which $R_3$ is halogen, for example, bromine, with copper-(I) cyanide in N-methylpyrrolidone, the halogen atom is exchanged for the nitrile group thus forming the 2-(p-cyanophenyl)-tetrahydroquinazolines of formula (I). In turn, the 2-(p-trifluoromethylphenyl)-tetrahydroquinazolines of the invention can be obtained from the cyano compounds by saponification to the corresponding carboxylic acids and reaction of the latter with sulphur tetrafluoride.

The liquid-crystalline dielectrics of this invention contain two or more components, including at least one of formula (I). The other components are preferably nematic or nematogenic substances from the classes of azobenzenes, azoxybenzenes, biphenyls, Schiff bases, in particular, benzylidene derivatives, phenyl benzoates, phenylpyrimidines, phenylcyclohexanes, optionally halogenated stilbenes, diphenylacetylene derivatives, diphenylnitrones and substituted cinnamic acids. The most important compounds which can be used as such further components, can be characterized by formula (V):

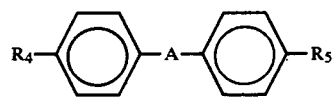

(V)

wherein A is

—CH=CH—

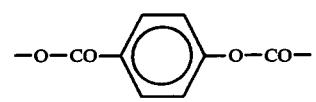

—CX'=CH—

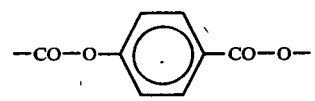

—CH=CX'—

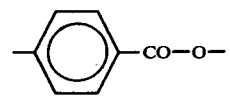

—C≡C—

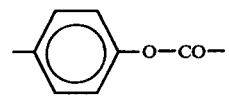

—N=N—

—N(O)=N—

—N=N(O)—
—O—CO—
—CO—O—
—S—CO—

—CO—S—

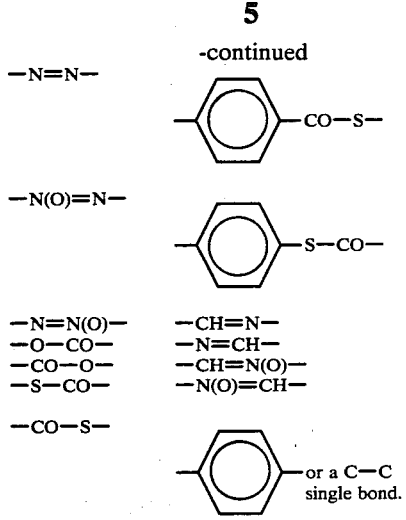

—CH=N—
—N=CH—
—CH=N(O)—
—N(O)=CH— or a C—C single bond.

Further possible components of the dielectrics of this invention include those compounds of formula (V) in which one or more phenyl rings are replaced by a corresponding number of trans-cyclohexyl rings; one of these rings can also be a 2,5-disubstituted pyrimidine ring.

X′ is halogen, preferably Cl, or —CN; $R_5$ and $R_4$ are identical or different and can be alkyl, alkoxy, alkanoyl, alkanoyloxy or alkoxycarbonyloxy radicals having up to 18, preferably up to 8, C atoms; moreover, one of these radicals can also be —CN, —NC, $NO_2$, $CF_3$ or halogen.

In most of these compounds, $R_5$ and $R_4$ are preferably different, one of the radicals being an alkyl or alkoxy group in most cases. A large number of other variants of the envisaged substituents, however, are also common. Many such substances are commercially available.

The dielectrics of this invention contain as a rule at least 30, preferably 50–99, in particular 60–98, percent by weight of the compounds of the formulae (I) and (V). Of this, preferably 5–50 percent by weight, in particular 10–30 percent by weight, is constituted by one or more compounds of formula (I). The present invention also comprises those liquid-crystalline dielectrics to which only less than 5 percent by weight, for example, 0.1 to 3 percent by weight, of one or more compounds of formula (I) have been added, for example, for doping purposes.

The preparation of the dielectrics of this invention is carried out in a manner conventional per se. As a rule, the desired quantity of the components used in a smaller quantity is dissolved in the components representing the main constituent, advantageously at elevated temperature. If a temperature above the clear point of the main constituent is used, the completeness of the solution process can be observed with particular ease.

It is also possible, however, to mix solutions of the components of formulae (I) and (V) in a suitable organic solvent, for example, acetone, chloroform or methanol, and, after thorough mixing, to remove the solvent, for example, by distillation under reduced pressure. Of course, it is necessary in this procedure to take care that no impurities or undesired doping substances are introduced by the solvent.

The liquid-crystalline dielectrics of this invention can be modified by suitable additives in such a way that they can be used in all hitherto disclosed types of liquid crystal display elements. Additives of this type are known to those skilled in the art and are extensively described in the relevant literature. For example, substances can be added for varying the viscosity, the conductivity and/or the orientation of the nematic phases. Substances of this type are described, for example, in German Offenlegungsschriften Nos. 2,209,127; 2,338,281; 2,450,088; 2,548,360 and 2,637,430.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point, of a liquid-crystalline substance in degrees Centigrade; boiling points are marked b.p.

EXAMPLE 1

2.46 g of 4-n-hexyl-2-hydroxymethylene-cyclohexanone and 3.1 g of 4-n-butoxy-benzamidine hydrochloride are added one after the other to a solution of 0.3 g of sodium in 14 ml of ethanol and the reaction mixture is heated to the boil for 4 hours, with stirring. Subsequently, the ethanol is distilled off, 50 ml of water is added to the residue and the aqueous reaction mixture is extracted twice with 50 ml of diethyl ether. The extracts are dried over sodium sulphate and evaporated. The remaining 2-(4-n-butoxyphenyl)-6-n-hexyl-5,6,7,8-tetrahydroquinazoline is recrystallized from ethanol; yield 2.2 g, m.p. 73°, c.p. 105°.

The following are prepared analogously:

2-(4-Methylphenyl)-6-methyl-5,6,7,8-tetrahydroquinazoline,
2-(4-Methylphenyl)-6-ethyl-5,6,7,8-tetrahydroquinazoline,
2-(4-Methylphenyl)-6-n-propyl-5,6,7,8-tetrahydroquinazoline,
2-(4-Methylphenyl)-6-n-butyl-5,6,7,8-tetrahydroquinazoline,
2-(4-Methylphenyl)-6-n-pentyl-5,6,7,8-tetrahydroquinazoline,
2-(4-Methylphenyl)-6-n-hexyl-5,6,7,8-tetrahydroquinazoline,
2-(4-Methylphenyl)-6-n-heptyl-5,6,7,8-tetrahydroquinazoline,
2-(4-Methylphenyl)-6-n-octyl-5,6,7,8-tetrahydroquinazoline,
2-(4-Methylphenyl)-6-n-nonyl-5,6,7,8-tetrahydroquinazoline,
2-(4-Methylphenyl)-6-n-decyl-5,6,7,8-tetrahydroquinazoline,
2-(4-Methylphenyl)-6-(2-methylbutyl)-5,6,7,8-tetrahydroquinazoline,
2-(4-Methylphenyl)-6-(2-ethylhexyl)-5,6,7,8-tetrahydroquinazoline, 2-(4-Ethylphenyl)-6-methyl-5,6,7,8-tetrahydroquinazoline,
2-(4-Ethylphenyl)-6-ethyl-5,6,7,8-tetrahydroquinazoline,
2-(4-Ethylphenyl)-6-n-propyl-5,6,7,8-tetrahydroquinazoline, 2-(4-Ethylphenyl)-6-n-butyl-5,6,7,8-tetrahydroquinazoline,
2-(4-Ethylphenyl)-6-n-pentyl-5,6,7,8-tetrahydroquinazoline,
2-(4-Ethylphenyl)-6-n-hexyl-5,6,7,8-tetrahydroquinazoline,
2-(4-Ethylphenyl)-6-n-heptyl-5,6,7,8-tetrahydroquinazoline,
2-(4-Ethylphenyl)-6-n-octyl-5,6,7,8-tetrahydroquinazoline,
2-(4-Ethylphenyl)-6-n-nonyl-5,6,7,8-tetrahydroquinazoline,
2-(4-Ethylphenyl)-6-n-decyl-5,6,7,8-tetrahydroquinazoline,
2-(4-Ethylphenyl)-6-(2-methylbutyl)-5,6,7,8-tetrahydroquinazoline,
2-(4-Ethylphenyl)-6-(2-ethylhexyl)-5,6,7,8-tetrahydroquinazoline, 2-(4-n-Propylphenyl)-6-methyl-5,6,7,8-tetrahydroquinazoline,
2-(4-n-Propylphenyl)-6-ethyl-5,6,7,8-tetrahydroquinazoline,
2-(4-n-Propylphenyl)-6-n-propyl-5,6,7,8-tetrahydroquinazoline,
2-(4-n-Propylphenyl)-6-n-butyl-5,6,7,8-tetrahydroquinazoline,
2-(4-n-Propylphenyl)-6-n-pentyl-5,6,7,8-tetrahydroquinazoline,
2-(4-n-Propylphenyl)-6-n-hexyl-5,6,7,8-tetrahydroquinazoline,
2-(4-n-Propylphenyl)-6-n-heptyl-5,6,7,8-tetrahydroquinazoline,
2-(4-n-Propylphenyl)-6-n-octyl-5,6,7,8-tetrahydroquinazoline,
2-(4-n-Propylphenyl)-6-n-nonyl-5,6,7,8-tetrahydroquinazoline,
2-(4-n-Propylphenyl)-6-n-decyl-5,6,7,8-tetrahydroquinazoline,
2-(4-n-Propylphenyl)-6-(2-methylbutyl)-5,6,7,8-tetrahydroquinazoline,
2-(4-n-Propylphenyl)-6-(2-ethylhexyl)-5,6,7,8-tetrahydroquinazoline, 2-(4-n-Butylphenyl)-6-methyl-5,6,7,8-tetrahydroquinazoline,
2-(4-n-Butylphenyl)-6-ethyl-5,6,7,8-tetrahydroquinazoline,
2-(4-n-Butylphenyl)-6-n-propyl-5,6,7,8-tetrahydroquinazoline,
2-(4-n-Butylphenyl)-6-n-butyl-5,6,7,8-tetrahydroquinazoline,
2-(4-n-Butylphenyl)-6-n-pentyl-5,6,7,8-tetrahydroquinazoline,
2-(4-n-Butylphenyl)-6-n-hexyl-5,6,7,8-tetrahydroquinazoline,
2-(4-n-Butylphenyl)-6-n-heptyl-5,6,7,8-tetrahydroquinazoline,
2-(4-n-Butylphenyl)-6-n-octyl-5,6,7,8-tetrahydroquinazoline,
2-(4-n-Butylphenyl)-6-n-nonyl-5,6,7,8-tetrahydroquinazoline,
2-(4-n-Butylphenyl)-6-n-decyl-5,6,7,8-tetrahydroquinazoline,
2-(4-n-Butylphenyl)-6-(2-methylbutyl)-5,6,7,8-tetrahydroquinazoline,
2-(4-n-Butylphenyl)-6-(2-ethylhexyl)-5,6,7,8-tetrahydroquinazoline, 2-(4-n-Pentylphenyl)-6-methyl-5,6,7,8-tetrahydroquinazoline,
2-(4-n-Pentylphenyl)-6-ethyl-5,6,7,8-tetrahydroquinazoline,
2-(4-n-Pentylphenyl)-6-n-propyl-5,6,7,8-tetrahydroquinazoline,
2-(4-n-Pentylphenyl)-6-n-butyl-5,6,7,8-tetrahydroquinazoline,
2-(4-n-Pentylphenyl)-6-n-pentyl-5,6,7,8-tetrahydroquinazoline,
2-(4-n-Pentylphenyl)-6-n-hexyl-5,6,7,8-tetrahydroquinazoline,
2-(4-n-Pentylphenyl)-6-n-heptyl-5,6,7,8-tetrahydroquinazoline,
2-(4-n-Pentylphenyl)-6-n-octyl-5,6,7,8-tetrahydroquinazoline,
2-(4-n-Pentylphenyl)-6-n-nonyl-5,6,7,8-tetrahydroquinazoline,
2-(4-n-Pentylphenyl)-6-n-decyl-5,6,7,8-tetrahydroquinazoline,
2-(4-n-Pentylphenyl)-6-(2-methylbutyl)-5,6,7,8-tetrahydroquinazoline,
2-(4-n-Pentylphenyl)-6-(2-ethylhexyl)-5,6,7,8-tetrahydroquinazoline, 2-(4-n-Hexylphenyl)-6-methyl-5,6,7,8-tetrahydroquinazoline,
2-(4-n-Hexylphenyl)-6-ethyl-5,6,7,8-tetrahydroquinazoline,
2-(4-n-Hexylphenyl)-6-n-propyl-5,6,7,8-tetrahydroquinazoline,
2-(4-n-Hexylphenyl)-6-n-butyl-5,6,7,8-tetrahydroquinazoline,
2-(4-n-Hexylphenyl)-6-n-pentyl-5,6,7,8-tetrahydroquinazoline,
2-(4-n-Hexylphenyl)-6-n-hexyl-5,6,7,8-tetrahydroquinazoline,
2-(4-n-Hexylphenyl)-6-n-heptyl-5,6,7,8-tetrahydroquinazoline,
2-(4-n-Hexylphenyl)-6-n-octyl-5,6,7,8-tetrahydroquinazoline,
2-(4-n-Hexylphenyl)-6-n-nonyl-5,6,7,8-tetrahydroquinazoline,
2-(4-n-Hexylphenyl)-6-n-decyl-5,6,7,8-tetrahydroquinazoline,
2-(4-n-Hexylphenyl)-6-(2-methylbutyl)-5,6,7,8-tetrahydroquinazoline,
2-(4-n-Hexylphenyl)-6-(2-ethylhexyl)-5,6,7,8-tetrahydroquinazoline, 2-(4-n-Heptylphenyl)-6-methyl-5,6,7,8-tetrahydroquinazoline,
2-(4-n-Heptylphenyl)-6-ethyl-5,6,7,8-tetrahydroquinazoline,
2-(4-n-Heptylphenyl)-6-n-propyl-5,6,7,8-tetrahydroquinazoline,
2-(4-n-Heptylphenyl)-6-n-butyl-5,6,7,8-tetrahydroquinazoline,
2-(4-n-Heptylphenyl)-6-n-pentyl-5,6,7,8-tetrahydroquinazoline,
2-(4-n-Heptylphenyl)-6-n-hexyl-5,6,7,8-tetrahydroquinazoline,
2-(4-n-Heptylphenyl)-6-n-heptyl-5,6,7,8-tetrahydroquinazoline,
2-(4-n-Heptylphenyl)-6-n-octyl-5,6,7,8-tetrahydroquinazoline, 2-(4-n-Heptylphenyl)-6-n-nonyl-5,6,7,8-tetrahydroquinazoline,
2-(4-n-Heptylphenyl)-6-(2-methylbutyl)-5,6,7,8-tetrahydroquinazoline,
2-(4-n-Heptylphenyl)-6-(2-ethylhexyl)-5,6,7,8-tetrahydroquinazoline, 2-(4-n-Octylphenyl)-6-methyl-5,6,7,8-tetrahydroquinazoline,
2-(4-n-Octylphenyl)-6-ethyl-5,6,7,8-tetrahydroquinazoline,
2-(4-n-Octylphenyl)-6-n-propyl-5,6,7,8-tetrahydroquinazoline,
2-(4-n-Octylphenyl)-6-n-butyl-5,6,7,8-tetrahydroquinazoline,
2-(4-n-Octylphenyl)-6-n-pentyl-5,6,7,8-tetrahydroquinazoline,
2-(4-n-Octylphenyl)-6-n-hexyl-5,6,7,8-tetrahydroquinazoline,
2-(4-n-Octylphenyl)-6-n-heptyl-5,6,7,8-tetrahydroquinazoline,
2-(4-n-Octylphenyl)-6-n-octyl-5,6,7,8-tetrahydroquinazoline,
2-(4-n-Octylphenyl)-6-(2-methylbutyl)-5,6,7,8-tetrahydroquinazoline,
2-(4-n-Octylphenyl)-6-(2-ethylhexyl)-5,6,7,8-tetrahydroquinazoline, 2-[4-(2-Methylbutyl)-phenyl]-6-methyl-5,6,7,8-tetrahydroquinazoline,
2-[4-(2-Methylbutyl)-phenyl]-6-ethyl-5,6,7,8-tetrahydroquinazoline,
2-[4-(2-Methylbutyl)-phenyl]-6-n-propyl-5,6,7,8-tetrahydroquinazoline,
2-[4-(2-Methylbutyl)-phenyl]-6-n-butyl-5,6,7,8-tetrahydroquinazoline,
2-[4-(2-Methylbutyl)-phenyl]-6-n-pentyl-5,6,7,8-tetrahydroquinazoline,
2-[4-(2-Methylbutyl)-phenyl]-6-n-hexyl-5,6,7,8-tetrahydroquinazoline,
2-[4-(2-Methylbutyl)-phenyl]-6-n-heptyl-5,6,7,8-tetrahydroquinazoline,
2-[4-(2-Methylbutyl)-phenyl]-6-n-octyl-5,6,7,8-tetrahydroquinazoline,
2-[4-(2-Methylbutyl)-phenyl]-6-n-nonyl-5,6,7,8-tetrahydroquinazoline,
2-[4-(2-Methylbutyl)-phenyl]-6-n-decyl-5,6,7,8-tetrahydroquinazoline, 2-[4-(1-Methylheptyl)-phenyl]-6-methyl-5,6,7,8-tetrahydroquinazoline,
2-[4-(1-Methylheptyl)-phenyl]-6-ethyl-5,6,7,8-tetrahydroquinazoline,
2-[4-(1-Methylheptyl)-phenyl]-6-n-propyl-5,6,7,8-tetrahydroquinazoline,
2-[4-(1-Methylheptyl)-phenyl]-6-n-butyl-5,6,7,8-tetrahydroquinazoline,
2-[4-(1-Methylheptyl)-phenyl]-6-n-pentyl-5,6,7,8-tetrahydroquinazoline,
2-[4-(1-Methylheptyl)-phenyl]-6-n-hexyl-5,6,7,8-tetrahydroquinazoline,
2-[4-(1-Methylheptyl)-phenyl]-6-n-heptyl-5,6,7,8-tetrahydroquinazoline,
2-[4-(1-Methylheptyl)-phenyl]-6-n-octyl-5,6,7,8-tetrahydroquinazoline,
2-[4-(1-Methylheptyl)-phenyl]-6-n-nonyl-5,6,7,8-tetrahydroquinazoline,
2-[4-(1-Methylheptyl)-phenyl]-6-n-decyl-5,6,7,8-tetrahydroquinzoline, 2-(4-Methoxyphenyl)-6-methyl-5,6,7,8-tetrahydroquinazoline,
2-(4-Methoxyphenyl)-6-ethyl-5,6,7,8-tetrahydroquinazoline,
2-(4-Methoxyphenyl)-6-n-propyl-5,6,7,8-tetrahydroquinazoline,
2-(4-Methoxyphenyl)-6-n-butyl-5,6,7,8-tetrahydroquinazoline,
2-(4-Methoxyphenyl)-6-n-pentyl-5,6,7,8-tetrahydroquinazoline,
2-(4-Methoxyphenyl)-6-n-hexyl-5,6,7,8-tetrahydroquinazoline,
2-(4-Methoxyphenyl)-6-n-heptyl-5,6,7,8-tetrahydroquinazoline,
2-(4-Methoxyphenyl)-6-n-octyl-5,6,7,8-tetrahydroquinazoline,
2-(4-Methoxyphenyl)-6-n-nonyl-5,6,7,8-tetrahydroquinazoline,
2-(4-Methoxyphenyl)-6-n-decyl-5,6,7,8-tetrahydroquinazoline,
2-(4-Methoxyphenyl)-6-(2-methylbutyl)-5,6,7,8-tetrahydroquinazoline,
2-(4-Methoxyphenyl)-6-(2-ethylhexyl)-5,6,7,8-tetrahydroquinazoline, 2-(4-Ethoxyphenyl)-6-methyl-5,6,7,8-tetrahydroquinazoline,
2-(4-Ethoxyphenyl)-6-ethyl-5,6,7,8-tetrahydroquinazoline,
2-(4-Ethoxyphenyl)-6-n-propyl-5,6,7,8-tetrahydroquinazoline,
2-(4-Ethoxyphenyl)-6-n-butyl-5,6,7,8-tetrahydroquinazoline,
2-(4-Ethoxyphenyl)-6-n-pentyl-5,6,7,8-tetrahydroquinazoline,
2-(4-Ethoxyphenyl)-6-n-hexyl-5,6,7,8-tetrahydroquinazoline,
2-(4-Ethoxyphenyl)-6-n-heptyl-5,6,7,8-tetrahydroquinazoline,
2-(4-Ethoxyphenyl)-6-n-octyl-5,6,7,8-tetrahydroquinazoline,
2-(4-Ethoxyphenyl)-6-n-nonyl-5,6,7,8-tetrahydroquinazoline,
2-(4-Ethoxyphenyl)-6-n-decyl-5,6,7,8-tetrahydroquinazoline,
2-(4-Ethoxyphenyl)-6-(2-methylbutyl)-5,6,7,8-tetrahydroquinazoline,
2-(4-Ethoxyphenyl)-6-(2-ethylhexyl)-5,6,7,8-tetrahydroquinazoline, 2-(4-n-Propoxyphenyl)-6-methyl-5,6,7,8-tetrahydroquinazoline,
2-(4-n-Propoxyphenyl)-6-ethyl-5,6,7,8-tetrahydroquinazoline,
2-(4-n-Propoxyphenyl)-6-n-propyl-5,6,7,8-tetrahydroquinazoline,
2-(4-n-Propoxyphenyl)-6-n-butyl-5,6,7,8-tetrahydroquinazoline,
2-(4-n-Propoxyphenyl)-6-n-pentyl-5,6,7,8-tetrahydroquinazoline,
2-(4-n-Propoxyphenyl)-6-n-hexyl-5,6,7,8-tetrahydroquinazoline,
2-(4-n-Propoxyphenyl)-6-n-heptyl-5,6,7,8-tetrahydroquinazoline, 2-(4-n-Propoxyphenyl)-6-n-octyl-5,6,7,8-tetrahydroquinazoline,
2-(4-n-Propoxyphenyl)-6-n-nonyl-5,6,7,8-tetrahydroquinazoline,
2-(4-n-Propoxyphenyl)-6-n-decyl-5,6,7,8-tetrahydroquinazoline,
2-(4-n-Propoxyphenyl)-6-(2-methylbutyl)-5,6,7,8-tetrahydroquinazoline,
2-(4-n-Propoxyphenyl)-6-(2-ethylhexyl)-5,6,7,8-tetrahydroquinazoline, 2-(4-n-Butoxyphenyl)-6-methyl-5,6,7,8-tetrahydroquinazoline,
2-(4-n-Butoxyphenyl)-6-ethyl-5,6,7,8-tetrahydroquinazoline,
2-(4-n-Butoxyphenyl)-6-n-propyl-5,6,7,8-tetrahydroquinazoline,
2-(4-n-Butoxyphenyl)-6-n-butyl-5,6,7,8-tetrahydroquinazoline,
2-(4-n-Butoxyphenyl)-6-n-pentyl-5,6,7,8-tetrahydroquinazoline,
2-(4-n-Butoxyphenyl)-6-n-heptyl-5,6,7,8-tetrahydroquinazoline,
2-(4-n-Butoxyphenyl)-6-n-octyl-5,6,7,8-tetrahydroquinazoline,
2-(4-n-Butoxyphenyl)-6-n-nonyl-5,6,7,8-tetrahydroquinazoline,
2-(4-n-Butoxyphenyl)-6-n-decyl-5,6,7,8-tetrahydroquinazoline,
2-(4-n-Butoxyphenyl)-6-(2-methylbutyl)-5,6,7,8-tetrahydroquinazoline,
2-(4-n-Butoxyphenyl)-6-(2-ethylhexyl)-5,6,7,8-tetrahydroquinazoline, 2-(4-n-Pentyloxyphenyl)-6-methyl-5,6,7,8-tetrahydroquinazoline,
2-(4-n-Pentyloxyphenyl)-6-ethyl-5,6,7,8-tetrahydroquinazoline,
2-(4-n-Pentyloxyphenyl)-6-n-propyl-5,6,7,8-tetrahydroquinazoline,
2-(4-n-Pentyloxyphenyl)-6-n-butyl-5,6,7,8-tetrahydroquinazoline,
2-(4-n-Pentyloxyphenyl)-6-n-pentyl-5,6,7,8-tetrahydroquinazoline,
2-(4-n-Pentyloxyphenyl)-6-n-hexyl-5,6,7,8-tetrahydroquinazoline,
2-(4-n-Pentyloxyphenyl)-6-n-heptyl-5,6,7,8-tetrahydroquinazoline,
2-(4-n-Pentyloxyphenyl)-6-n-octyl-5,6,7,8-tetrahydroquinazoline,
2-(4-n-Pentyloxyphenyl)-6-n-nonyl-5,6,7,8-tetrahydroquinazoline,
2-(4-n-Pentyloxyphenyl)-6-n-decyl-5,6,7,8-tetrahydroquinazoline,
2-(4-n-Pentyloxyphenyl)-6-(2-methylbutyl)-5,6,7,8-tetrahydroquinazoline,
2-(4-n-Pentyloxyphenyl)-6-(2-ethoxyphenyl)-5,6,7,8-tetrahydroquinazoline, 2-(4-n-Hexyloxyphenyl)-6-methyl-5,6,7,8-tetrahydroquinazoline,
2-(4-n-Hexyloxyphenyl)-6-ethyl-5,6,7,8-tetrahydroquinazoline,
2-(4-n-Hexyloxyphenyl)-6-n-propyl-5,6,7,8-tetrahydroquinazoline,
2-(4-n-Hexyloxyphenyl)-6-n-butyl-5,6,7,8-tetrahydroquinazoline,
2-(4-n-Hexyloxyphenyl)-6-n-pentyl-5,6,7,8-tetrahydroquinazoline,
2-(4-n-Hexyloxyphenyl)-6-n-hexyl-5,6,7,8-tetrahydroquinazoline,
2-(4-n-Hexyloxyphenyl)-6-n-heptyl-5,6,7,8-tetrahydroquinazoline,
2-(4-n-Hexyloxyphenyl)-6-n-octyl-5,6,7,8-tetrahydroquinazoline,
2-(4-n-Hexyloxyphenyl)-6-n-nonyl-5,6,7,8-tetrahydroquinazoline,
2-(4-n-Hexyloxyphenyl)-6-n-decyl-5,6,7,8-tetrahydroquinazoline,
2-(4-n-Hexyloxyphenyl)-6-(2-methylbutyl)-5,6,7,8-tetrahydroquinazoline,
2-(4-n-Hexyloxyphenyl)-6-(2-ethylhexyl)-5,6,7,8-tetrahydroquinazoline, 2-(4-n-Heptyloxyphenyl)-6-methyl-5,6,7,8-tetrahydroquinazoline,
2-(4-n-Heptyloxyphenyl)-6-ethyl-5,6,7,8-tetrahydroquinazoline,
2-(4-n-Heptyloxyphenyl)-6-n-propyl-5,6,7,8-tetrahydroquinazoline,
2-(4-n-Heptyloxyphenyl)-6-n-butyl-5,6,7,8-tetrahydroquinazoline,
2-(4-n-Heptyloxyphenyl)-6-n-pentyl-5,6,7,8-tetrahydroquinazoline,
2-(4-n-Heptyloxyphenyl)-6-n-hexyl-5,6,7,8-tetrahydroquinazoline,
2-(4-n-Heptyloxyphenyl)-6-n-heptyl-5,6,7,8-tetrahydroquinazoline,
2-(4-n-Heptyloxyphenyl)-6-n-octyl-5,6,7,8-tetrahydroquinazoline,
2-(4-n-Heptyloxyphenyl)-6-n-nonyl-5,6,7,8-tetrahydroquinazoline,
2-(4-n-Heptyloxyphenyl)-6-(2-methylbutyl)-5,6,7,8-tetrahydroquinazoline,
2-(4-n-Heptyloxyphenyl)-6-(2-ethylhexyl)-5,6,7,8-tetrahydroquinazoline, 2-(4-n-Octyloxyphenyl)-6-methyl-5,6,7,8-tetrahydroquinazoline,
2-(4-n-Octyloxyphenyl)-6-ethyl-5,6,7,8-tetrahydroquinazoline,
2-(4-n-Octyloxyphenyl)-6-n-propyl-5,6,7,8-tetrahydroquinazoline,
2-(4-n-Octyloxyphenyl)-6-n-butyl-5,6,7,8-tetrahydroquinazoline,
2-(4-n-Octyloxyphenyl)-6-n-pentyl-5,6,7,8-tetrahydroquinazoline,
2-(4-n-Octyloxyphenyl)-6-n-hexyl-5,6,7,8-tetrahydroquinazoline,
2-(4-n-Octyloxyphenyl)-6-n-heptyl-5,6,7,8-tetrahydroquinazoline,
2-(4-n-Octyloxyphenyl)-6-n-octyl-5,6,7,8-tetrahydroquinazoline,
2-(4-n-Octyloxyphenyl)-6-(2-methylbutyl)-5,6,7,8-tetrahydroquinazoline,
2-(4-n-Octyloxyphenyl)-6-(2-ethylhexyl)-5,6,7,8-tetrahydroquinazoline, 2-[4-(2-Ethylhexyloxy)-phenyl]-6-methyl-5,6,7,8-tetrahydroquinazoline,
2-[4-(2-Ethylhexyloxy)-phenyl]-6-ethyl-5,6,7,8-tetrahydroquinazoline,
2-[4-(2-Ethylhexyloxy)-phenyl]-6-n-propyl-5,6,7,8-tetrahydroquinazoline, 2-[4-(2-Ethylhexyloxy)-phenyl]-6-n-butyl-5,6,7,8-tetrahydroquinazoline,
2-[4-(2-Ethylhexyloxy)-phenyl]-6-n-pentyl-5,6,7,8-tetrahydroquinazoline,
2-[4-(2-Ethylhexyloxy)-phenyl]-6-n-hexyl-5,6,7,8-tetrahydroquinazoline,
2-[4-(2-Ethylhexyloxy)-phenyl]-6-n-heptyl-5,6,7,8-tetrahydroquinazoline,
2-[4-(2-Ethylhexyloxy)-phenyl]-6-n-octyl-5,6,7,8-tetrahydroquinazoline,
2-[4-(2-Ethylhexyloxy)-phenyl]-6-n-nonyl-5,6,7,8-tetrahydroquinazoline, 2-(4-Chlorophenyl)-6-methyl-5,6,7,8-tetrahydroquinazoline,
2-(4-Chlorophenyl)-6-ethyl-5,6,7,8-tetrahydroquinazoline,
2-(4-Chlorophenyl)-6-n-propyl-5,6,7,8-tetrahydroquinazoline,
2-(4-Chlorophenyl)-6-n-butyl-5,6,7,8-tetrahydroquinazoline,
2-(4-Chlorophenyl)-6-n-pentyl-5,6,7,8-tetrahydroquinazoline,
2-(4-Chlorophenyl)-6-n-hexyl-5,6,7,8-tetrahydroquinazoline,
2-(4-Chlorophenyl)-6-n-heptyl-5,6,7,8-tetrahydroquinazoline,
2-(4-Chlorophenyl)-6-n-octyl-5,6,7,8-tetrahydroquinazoline,
2-(4-Chlorophenyl)-6-n-nonyl-5,6,7,8-tetrahydroquinazoline,
2-(4-Chlorophenyl)-6-n-decyl-5,6,7,8-tetrahydroquinazoline,
2-(4-Chlorophenyl)-6-(2-methylbutyl)-5,6,7,8-tetrahydroquinazoline,
2-(4-Chlorophenyl)-6-(2-ethylhexyl)-5,6,7,8-tetrahydroquinazoline, 2-(4-Bromophenyl)-6-methyl-5,6,7,8-tetrahydroquinazoline,
2-(4-Bromophenyl)-6-ethyl-5,6,7,8-tetrahydroquinazoline,
2-(4-Bromophenyl)-6-n-propyl-5,6,7,8-tetrahydroquinazoline,
2-(4-Bromophenyl)-6-n-butyl-5,6,7,8-tetrahydroquinazoline,
2-(4-Bromophenyl)-6-n-pentyl-5,6,7,8-tetrahydroquinazoline,
2-(4-Bromophenyl)-6-n-hexyl-5,6,7,8-tetrahydroquinazoline, m.p. 167°;
2-(4-Bromophenyl)-6-n-heptyl-5,6,7,8-tetrahydroquinazoline,
2-(4-Bromophenyl)-6-n-octyl-5,6,7,8-tetrahydroquinazoline,
2-(4-Bromophenyl)-6-n-nonyl-5,6,7,8-tetrahydroquinazoline,
2-(4-Bromophenyl)-6-n-decyl-5,6,7,8-tetrahydroquinazoline,
2-(4-Bromophenyl)-6-(2-methylbutyl)-5,6,7,8-tetrahydroquinazoline, 2-(4-Fluorophenyl)-6-methyl-5,6,7,8-tetrahydroquinazoline,
2-(4-Fluorophenyl)-6-ethyl-5,6,7,8-tetrahydroquinazoline,
2-(4-Fluorophenyl)-6-n-propyl-5,6,7,8-tetrahydroquinazoline,
2-(4-Fluorophenyl)-6-n-butyl-5,6,7,8-tetrahydroquinazoline,
2-(4-Fluorophenyl)-6-n-pentyl-5,6,7,8-tetrahydroquinazoline,
2-(4-Fluorophenyl)-6-n-hexyl-5,6,7,8-tetrahydroquinazoline,
2-(4-Fluorophenyl)-6-n-heptyl-5,6,7,8-tetrahydroquinazoline,
2-(4-Fluorophenyl)-6-n-octyl-5,6,7,8-tetrahydroquinazoline,
2-(4-Fluorophenyl)-6-n-nonyl-5,6,7,8-tetrahydroquinazoline,
2-(4-Fluorophenyl)-6-n-decyl-5,6,7,8-tetrahydroquinazoline,
2-(4-Fluorophenyl)-6-(2-methylbutyl)-5,6,7,8-tetrahydroquinazoline,
2-(4-Fluorophenyl)-6-(2-ethylhexyl)-5,6,7,8-tetrahydroquinazoline, 2-(4-Nitrophenyl)-6-methyl-5,6,7,8-tetrahydroquinazoline,
2-(4-Nitrophenyl)-6-ethyl-5,6,7,8-tetrahydroquinazoline,
2-(4-Nitrophenyl)-6-n-propyl-5,6,7,8-tetrahydroquinazoline,
2-(4-Nitrophenyl)-6-n-butyl-5,6,7,8-tetrahydroquinazoline,
2-(4-Nitrophenyl)-6-n-pentyl-5,6,7,8-tetrahydroquinazoline,
2-(4-Nitrophenyl)-6-n-hexyl-5,6,7,8-tetrahydroquinazoline,
2-(4-Nitrophenyl)-6-n-heptyl-5,6,7,8-tetrahydroquinazoline,
2-(4-Nitrophenyl)-6-n-octyl-5,6,7,8-tetrahydroquinazoline,
2-(4-Nitrophenyl)-6-n-nonyl-5,6,7,8-tetrahydroquinazoline,
2-(4-Nitrophenyl)-6-n-decyl-5,6,7,8-tetrahydroquinazoline,
2-(4-Nitrophenyl)-6-(2-methylbutyl)-5,6,7,8-tetrahydroquinazoline and
2-(4-Nitrophenyl)-6-(2-ethylhexyl)-5,6,7,8-tetrahydroquinazoline.

EXAMPLE 2

26.5 g of 2-(4-bromophenyl)-6-n-hexyl-5,6,7,8-tetrahydroquinazoline and 7.6 g of copper-(I) cyanide in 70 ml of N-methylpyrrolid-2-one are heated to 200° for 2.5 hours, with stirring. After cooling, the reaction mixture is poured into 300 ml of ice water and the precipitate thus forming is filtered off and washed with water. After drying, the black-gray precipitate is digested five times with 50 ml of diethyl ether and the ether filtrates are dried over sodium sulfate and evaporated. The remaining 2-(4-cyanophenyl)-6-n-hexyl-5,6,7,8-tetrahydroquinazoline is recrystallized from ethanol with the addition of active charcoal; yield 17.3 g of colorless crystals, m.p. 90°, c.p. 108°.

The following are prepared analogously:
2-(4-cyanophenyl)-6-methyl-5,6,7,8-tetrahydroquinazoline,
2-(4-cyanophenyl)-6-ethyl-5,6,7,8-tetrahydroquinazoline,
2-(4-cyanophenyl)-6-n-propyl-5,6,7,8-tetrahydroquinazoline,
2-(4-cyanophenyl)-6-n-butyl-5,6,7,8-tetrahydroquinazoline, 2-(4-cyanophenyl)-6-n-pentyl-5,6,7,8-tetrahydroquinazoline, m.p. 98°, c.p. 114°,
2-(4-cyanophenyl)-6-n-heptyl-5,6,7,8-tetrahydroquinazoline,
2-(4-cyanophenyl)-6-n-octyl-5,6,7,8-tetrahydroquinazoline,
2-(4-cyanophenyl)-6-n-nonyl-5,6,7,8-tetrahydroquinazoline,
2-(4-cyanophenyl)-6-n-decyl-5,6,7,8-tetrahydroquinazoline,
2-(4-cyanophenyl)-6-(2-methylbutyl)-5,6,7,8-tetrahydroquinazoline, and
2-(4-cyanophenyl)-6-(2-ethylhexyl)-5,6,7,8-tetrahydroquinazoline.

EXAMPLE 3

(a) 37.3 g of 2-(4-benzyloxyphenyl)-6-n-butyl-5,6,7,8-tetrahydroquinazoline is hydrogenated in 300 ml of methanol at 60° under normal pressure in the presence of 10 g of palladium-on-active charcoal (5% of Pd), until the absorption of hydrogen ceases. The catalyst is then filtered off, the filtrate is evaporated and the remaining 2-(4-hydroxyphenyl)-6-n-butyl-5,6,7,8-tetrahydroquinazoline is recrystallized from ethanol; yield 21.6 g.

The following were prepared analogously:
2-(4-hydroxyphenyl)-6-methyl-5,6,7,8-tetrahydroquinazoline,
2-(4-hydroxyphenyl)-6-ethyl-5,6,7,8-tetrahydroquinazoline,
2-(4-hydroxyphenyl)-6-n-propyl-5,6,7,8-tetrahydroquinazoline,
2-(4-hydroxyphenyl)-6-n-pentyl-5,6,7,8-tetrahydroquinazoline,
2-(4-hydroxyphenyl)-6-n-hexyl-5,6,7,8-tetrahydroquinazoline,
2-(4-hydroxyphenyl)-6-n-heptyl-5,6,7,8-tetrahydroquinazoline,
2-(4-hydroxyphenyl)-6-n-octyl-5,6,7,8-tetrahydroquinazoline,
2-(4-hydroxyphenyl)-6-n-nonyl-5,6,7,8-tetrahydroquinazoline,
2-(4-hydroxyphenyl)-6-n-decyl-5,6,7,8-tetrahydroquinazoline,
2-(4-hydroxyphenyl)-6-(2-methylbutyl)-5,6,7,8-tetrahydroquinazoline, and
2-(4-hydroxyphenyl)-6-(2-ethylhexyl)-5,6,7,8-tetrahydroquinazoline.

(b) 6.7 g of n-hexanoyl chloride is added dropwise at 100° and with stirring, to a solution of 11.3 g of 2-(4-hydroxyphenyl)-6-n-butyl-5,6,7,8-tetrahydroquinazoline and 4 g of pyridine in 100 ml of toluene. After further stirring for two hours, the reaction mixture is filtered while still hot, the pyridine hydrochloride which has been filtered off is rinsed with 50 ml of toluene and the combined filtrates are evaporated. The remaining 2-(4-n-hexanoyloxyphenyl)-6-n-butyl-5,6,7,8-tetrahydroquinazoline is recrystallized from ethyl acetate; yield 15.3 g of colorless crystals.

The following are prepared analogously:
2-(4-acetoxyphenyl)-6-methyl-5,6,7,8-tetrahydroquinazoline,
2-(4-acetoxyphenyl)-6-ethyl-5,6,7,8-tetrahydroquinazoline,
2-(4-acetoxyphenyl)-6-n-propyl-5,6,7,8-tetrahydroquinazoline,
2-(4-acetoxyphenyl)-6-n-butyl-5,6,7,8-tetrahydroquinazoline,
2-(4-acetoxyphenyl)-6-n-pentyl-5,6,7,8-tetrahydroquinazoline,
2-(4-acetoxyphenyl)-6-n-hexyl-5,6,7,8-tetrahydroquinazoline,
2-(4-acetoxyphenyl)-6-n-heptyl-5,6,7,8-tetrahydroquinazoline,
2-(4-Acetoxyphenyl)-6-n-octyl-5,6,7,8-tetrahydroquinazoline,
2-(4-Acetoxyphenyl)-6-n-nonyl-5,6,7,8-tetrahydroquinazoline,
2-(4-Acetoxyphenyl)-6-n-decyl-5,6,7,8-tetrahydroquinazoline,
2-(4-Acetoxyphenyl)-6-(2-methylbutyl)-5,6,7,8-tetrahydroquinazoline and
2-(4-Acetoxyphenyl)-6-(2-ethylhexyl)-5,6,7,8-tetrahydroquinazoline.

2-(4-Propionyloxyphenyl)-6-methyl-5,6,7,8-tetrahydroquinazoline,
2-(4-Propionyloxyphenyl)-6-ethyl-5,6,7,8-tetrahydroquinazoline,
2-(4-Propionyloxyphenyl)-6-n-propyl-5,6,7,8-tetrahydroquinazoline,
2-(4-Propionyloxyphenyl)-6-n-butyl-5,6,7,8-tetrahydroquinazoline,
2-(4-Propionyloxyphenyl)-6-n-pentyl-5,6,7,8-tetrahydroquinazoline,
2-(4-Propionyloxyphenyl)-6-n-hexyl-5,6,7,8-tetrahydroquinazoline,
2-(4-Propionyloxyphenyl)-6-n-heptyl-5,6,7,8-tetrahydroquinazoline,
2-(4-Propionyloxyphenyl)-6-n-octyl-5,6,7,8-tetrahydroquinazoline,
2-(4-Propionyloxyphenyl)-6-n-nonyl-5,6,7,8-tetrahydroquinazoline,
2-(4-Propionyloxyphenyl)-6-n-decyl-5,6,7,8-tetrahydroquinazoline,
2-(4-Propionyloxyphenyl)-6-(2-methylbutyl)-5,6,7,8-tetrahydroquinazoline and
2-(4-Propionyloxyphenyl)-6-(2-ethylhexyl)-5,6,7,8-tetrahydroquinazoline.

2-(4-n-Butyryloxyphenyl)-6-methyl-5,6,7,8-tetrahydroquinazoline,
2-(4-n-Butyryloxyphenyl)-6-ethyl-5,6,7,8-tetrahydroquinazoline,
2-(4-n-Butyryloxyphenyl)-6-n-propyl-5,6,7,8-tetrahydroquinazoline,
2-(4-n-Butyryloxyphenyl)-6-n-butyl-5,6,7,8-tetrahydroquinazoline,
2-(4-n-Butyryloxyphenyl)-6-n-pentyl-5,6,7,8-tetrahydroquinazoline,
2-(4-n-Butyryloxyphenyl)-6-n-hexyl-5,6,7,8-tetrahydroquinazoline,
2-(4-n-Butyryloxyphenyl)-6-n-heptyl-5,6,7,8-tetrahydroquinazoline,
2-(4-n-Butyryloxyphenyl)-6-n-octyl-5,6,7,8-tetrahydroquinazoline,
2-(4-n-Butyryloxyphenyl)-6-n-nonyl-5,6,7,8-tetrahydroquinazoline,
2-(4-n-Butyryloxyphenyl)-6-n-decyl-5,6,7,8-tetrahydroquinazoline,
2-(4-n-Butyryloxyphenyl)-6-(2-methylbutyl)-5,6,7,8-tetrahydroquinazoline and
2-(4-n-Butyryloxyphenyl)-6-(2-ethylhexyl)-5,6,7,8-tetrahydroquinazoline, 2-(4-n-Pentanoyloxyphenyl)-6-methyl-5,6,7,8-tetrahydroquinazoline,
2-(4-n-Pentanoyloxyphenyl)-6-ethyl-5,6,7,8-tetrahydroquinazoline,
2-(4-n-Pentanoyloxyphenyl)-6-n-propyl-5,6,7,8-tetrahydroquinazoline,
2-(4-n-Pentanoyloxyphenyl)-6-n-butyl-5,6,7,8-tetrahydroquinazoline,
2-(4-n-Pentanoyloxyphenyl)-6-n-pentyl-5,6,7,8-tetrahydroquinazoline,
2-(4-n-Pentanoyloxyphenyl)-6-n-hexyl-5,6,7,8-tetrahydroquinazoline,
2-(4-n-Pentanoyloxyphenyl)-6-n-heptyl-5,6,7,8-tetrahydroquinazoline,
2-(4-n-Pentanoyloxyphenyl)-6-n-octyl-5,6,7,8-tetrahydroquinazoline,
2-(4-n-Pentanoyloxyphenyl)-6-n-nonyl-5,6,7,8-tetrahydroquinazoline,
2-(4-n-Pentanoyloxyphenyl)-6-n-decyl-5,6,7,8-tetrahydroquinazoline,
2-(4-n-Pentanoyloxyphenyl)-6-(2-methylbutyl)-5,6,7,8-tetrahydroquinazoline and
2-(4-n-Pentanoyloxyphenyl)-6-(2-ethylhexyl)-5,6,7,8-tetrahydroquinazoline,
2-(4-n-Hexanoyloxyphenyl)-6-methyl-5,6,7,8-tetrahydroquinazoline,
2-(4-n-Hexanoyloxyphenyl)-6-ethyl-5,6,7,8-tetrahydroquinazoline,
2-(4-n-Hexnanoyloxyphenyl)-6-n-propyl-5,6,7,8-tetrahydroquinazoline,
2-(4-n-Hexanoyloxyphenyl)-6-n-pentyl-5,6,7,8-tetrahydroquinazoline,
2-(4-n-Hexanoyloxyphenyl)-6-n-hexyl-5,6,7,8-tetrahydroquinazoline,
2-(4-n-Hexanoyloxyphenyl)-6-n-heptyl-5,6,7,8-tetrahydroquinazoline,
2-(4-n-Hexanoyloxyphenyl)-6-n-octyl-5,6,7,8-tetrahydroquinazoline,
2-(4-n-Hexanoyloxyphenyl)-6-n-nonyl-5,6,7,8-tetrahydroquinazoline,
2-(4-n-Hexanoyloxyphenyl)-6-n-decyl-5,6,7,8-tetrahydroquinazoline,
2-(4-n-Hexanoyloxyphenyl)-6-(2-methylbutyl)-5,6,7,8-tetrahydroquinazoline and
2-(4-n-Hexanoyloxyphenyl)-6-(2-ethylhexyl)-5,6,7,8-tetrahydroquinazoline, 2-(4-n-Heptanoyloxyphenyl)-6-methyl-5,6,7,8-tetrahydroquinazoline,
2-(4-n-Heptanoyloxyphenyl)-6-ethyl-5,6,7,8-tetrahydroquinazoline,
2-(4-n-Heptanoyloxyphenyl)-6-n-propyl-5,6,7,8-tetrahydroquinazoline,
2-(4-n-Heptanoyloxyphenyl)-6-n-butyl-5,6,7,8-tetrahydroquinazoline,
2-(4-n-Heptanoyloxyphenyl)-6-n-pentyl-5,6,7,8-tetrahydroquinazoline,
2-(4-n-Heptanoyloxyphenyl)-6-n-hexyl-5,6,7,8-tetrahydroquinazoline,
2-(4-n-Heptanoyloxyphenyl)-6-n-heptyl-5,6,7,8-tetrahydroquinazoline,
2-(4-n-Heptanoyloxyphenyl)-6-n-octyl-5,6,7,8-tetrahydroquinazoline,
2-(4-n-Heptanoyloxyphenyl)-6-n-nonyl-5,6,7,8-tetrahydroquinazoline,
2-(4-n-Heptanoyloxyphenyl)-6-n-decyl-5,6,7,8-tetrahydroquinazoline,
2-(4-n-Heptanoyloxyphenyl)-6-(2-methylbutyl)-5,6,7,8-tetrahydroquinazoline and
2-(4-n-Heptanoyloxyphenyl)-6-(2-ethylhexyl)-5,6,7,8-tetrahydroquinazoline, 2-(4-n-Octanoyloxyphenyl)-6-methyl-5,6,7,8-tetrahydroquinazoline,
2-(4-n-Octanoyloxyphenyl)-6-ethyl-5,6,7,8-tetrahydroquinazoline,
2-(4-n-Octanoyloxyphenyl)-6-n-propyl-5,6,7,8-tetrahydroquinazoline,
2-(4-n-Octanoyloxyphenyl)-6-n-butyl-5,6,7,8-tetrahydroquinazoline,
2-(4-n-Octanoyloxyphenyl)-6-n-pentyl-5,6,7,8-tetrahydroquinazoline,
2-(4-n-Octanoyloxyphenyl)-6-n-hexyl-5,6,7,8-tetrahydroquinazoline,
2-(4-n-Octanoyloxyphenyl)-6-n-heptyl-5,6,7,8-tetrahydroquinazoline,
2-(4-n-Octanoyloxyphenyl)-6-n-octyl-5,6,7,8-tetrahydroquinazoline,
2-(4-n-Octanoyloxyphenyl)-6-n-nonyl-5,6,7,8-tetrahydroquinazoline,
2-(4-n-Octanoyloxyphenyl)-6-n-decyl-5,6,7,8-tetrahydroquinazoline,
2-(4-n-Octanoyloxyphenyl)-6-(2-methylbutyl)-5,6,7,8-tetrahydroquinazoline and
2-(4-n-Octanoyloxyphenyl)-6-(2-ethylhexyl)-5,6,7,8-tetrahydroquinazoline, 2-(4-Ethoxycarbonyloxyphenyl)-6-methyl-5,6,7,8-tetrahydroquinazoline,
2-(4-Ethoxycarbonyloxyphenyl)-6-ethyl-5,6,7,8-tetrahydroquinazoline,
2-(4-Ethoxycarbonyloxyphenyl)-6-n-propyl-5,6,7,8-tetrahydroquinazoline,
2-(4-Ethoxycarbonyloxyphenyl)-6-n-butyl-5,6,7,8-tetrahydroquinazoline,
2-(4-Ethoxycarbonyloxyphenyl)-6-n-pentyl-5,6,7,8-tetrahydroquinazoline,
2-(4-Ethoxycarbonyloxyphenyl)-6-n-hexyl-5,6,7,8-tetrahydroquinazoline,
2-(4-Ethoxycarbonyloxyphenyl)-6-n-heptyl-5,6,7,8-tetrahydroquinazoline,
2-(4-Ethoxycarbonyloxyphenyl)-6-n-octyl-5,6,7,8-tetrahydroquinazoline,
2-(4-Ethoxycarbonyloxyphenyl)-6-n-nonyl-5,6,7,8-tetrahydroquinazoline,
2-(4-Ethoxycarbonyloxyphenyl)-6-n-decyl-5,6,7,8-tetrahydroquinazoline,
2-(4-Ethoxycarbonyloxyphenyl)-6-(2-methylbutyl)-5,6,7,8-tetrahydroquinazoline and
2-(4-Ethoxycarbonyloxyphenyl)-6-(2-ethylhexyl)-5,6,7,8-tetrahydroquinazoline, 2-(4-n-Propoxycarbonyloxyphenyl)-6-methyl-5,6,7,8-tetrahydroquinazoline,
2-(4-n-Propoxycarbonyloxyphenyl)-6-ethyl-5,6,7,8-tetrahydroquinazoline,
2-(4-n-Propoxycarbonyloxyphenyl)-6-n-propyl-5,6,7,8-tetrahydroquinazoline,
2-(4-n-Propoxycarbonyloxyphenyl)-6-n-butyl-5,6,7,8-tetrahydroquinazoline,
2-(4-n-Propoxycarbonyloxyphenyl)-6-n-pentyl-5,6,7,8-tetrahydroquinazoline,
2-(4-n-Propoxycarbonyloxyphenyl)-6-n-hexyl-5,6,7,8-tetrahydroquinazoline, 2-(4-n-Propoxycarbonyloxyphenyl)-6-n-heptyl-5,6,7,8-tetrahydroquinazoline,
2-(4-n-Propoxycarbonyloxyphenyl)-6-n-octyl-5,6,7,8-tetrahydroquinazoline,
2-(4-n-Propoxycarbonyloxyphenyl)-6-n-nonyl-5,6,7,8-tetrahydroquinazoline,
2-(4-n-Propoxycarbonyloxyphenyl)-6-n-decyl-5,6,7,8-tetrahydroquinazoline,
2-(4-n-Propoxycarbonyloxyphenyl)-6-(2-methylbutyl)-5,6,7,8-tetrahydroquinazoline and
2-(4-n-Propoxycarbonyloxyphenyl)-6-(ethylhexyl)-5,6,7,8-tetrahydroquinazoline, 2-(4-n-Butoxycarbonyloxyphenyl)-6-methyl-5,6,7,8-tetrahydroquinazoline,
2-(4-n-Butoxycarbonyloxyphenyl)-6-ethyl-5,6,7,8-tetrahydroquinazoline,
2-(4-n-Butoxycarbonyloxyphenyl)-6-n-propyl-5,6,7,8-tetrahydroquinazoline,
2-(4-n-Butoxycarbonyloxyphenyl)-6-n-butyl-5,6,7,8-tetrahydroquinazoline,
2-(4-n-Butoxycarbonyloxyphenyl)-6-n-pentyl-5,6,7,8-tetrahydroquinazoline,
2-(4-n-Butoxycarbonyloxyphenyl)-6-n-hexyl-5,6,7,8-tetrahydroquinazoline,
2-(4-n-Butoxycarbonyloxyphenyl)-6-n-heptyl-5,6,7,8-tetrahydroquinazoline,
2-(4-n-Butoxycarbonyloxyphenyl)-6-n-octyl-5,6,7,8-tetrahydroquinazoline,
2-(4-n-Butoxycarbonyloxyphenyl)-6-n-nonyl-5,6,7,8-tetrahydroquinazoline,
2-(4-n-Butoxycarbonyloxyphenyl)-6-n-decyl-5,6,7,8-tetrahydroquinazoline,
2-(4-n-Butoxycarbonyloxyphenyl)-6-(2-methylbutyl)-5,6,7,8-tetrahydroquinazoline and
2-(4-n-Butoxycarbonyloxyphenyl)-6-(2-ethylhexyl)-5,6,7,8-tetrahydroquinazoline, 2-(4-n-Pentyloxycarbonyloxyphenyl)-6-methyl-5,6,7,8-tetrahydroquinazoline,
2-(4-n-Pentyloxycarbonyloxyphenyl)-6-ethyl-5,6,7,8-tetrahydroquinazoline,
2-(4-n-Pentyloxycarbonyloxyphenyl)-6-n-propyl-5,6,7,8-tetrahydroquinazoline,
2-(4-n-Pentyloxycarbonyloxyphenyl)-6-n-butyl-5,6,7,8-tetrahydroquinazoline,
2-(4-n-Pentyloxycarbonyloxyphenyl)-6-n-pentyl-5,6,7,8-tetrahydroquinazoline,
2-(4-n-Pentyloxycarbonyloxyphenyl)-6-n-hexyl-5,6,7,8-tetrahydroquinazoline,
2-(4-n-Pentyloxycarbonyloxyphenyl)-6-n-heptyl-5,6,7,8-tetrahydroquinazoline,
2-(4-n-Pentyloxycarbonyloxyphenyl)-6-n-octyl-5,6,7,8-tetrahydroquinazoline,
2-(4-n-Pentyloxycarbonyloxyphenyl)-6-n-nonyl-5,6,7,8-tetrahydroquinazoline,
2-(4-n-Pentyloxycarbonyloxyphenyl)-6-n-decyl-5,6,7,8-tetrahydroquinazoline,
2-(4-n-Pentyloxycarbonyloxyphenyl)-6-(2-methylbutyl)-5,6,7,8-tetrahydroquinazoline and
2-(4-n-Pentyloxycarbonyloxyphenyl)-6-(2-ethylhexyl)-5,6,7,8-tetrahydroquinazoline.

2-(4-n-Hexyloxycarbonyloxyphenyl)-6-methyl-5,6,7,8-tetrahydroquinazoline,
2-(4-n-Hexyloxycarbonyloxyphenyl)-6-ethyl-5,6,7,8-tetrahydroquinazoline,
2-(4-n-Hexyloxycarbonyloxyphenyl)-6-n-propyl-5,6,7,8-tetrahydroquinazoline,
2-(4-n-Hexyloxycarbonyloxyphenyl)-6-n-butyl-5,6,7,8-tetrahydroquinazoline,
2-(4-n-Hexyloxycarbonyloxyphenyl)-6-n-pentyl-5,6,7,8-tetrahydroquinazoline,
2-(4-n-Hexyloxycarbonyloxyphenyl)-6-n-hexyl-5,6,7,8-tetrahydroquinazoline,
2-(4-n-Hexyloxycarbonyloxyphenyl)-6-n-heptyl-5,6,7,8-tetrahydroquinazoline,
2-(4-n-Hexyloxycarbonyloxyphenyl)-6-n-octyl-5,6,7,8-tetrahydroquinazoline,
2-(4-n-Hexyloxycarbonyloxyphenyl)-6-n-nonyl-5,6,7,8-tetrahydroquinazoline,
2-(4-n-Hexyloxycarbonyloxyphenyl)-6-n-decyl-5,6,7,8-tetrahydroquinazoline,
2-(4-n-Hexyloxycarbonyloxyphenyl)-6-(2-methylbutyl)-5,6,7,8-tetrahydroquinazoline and
2-(4-n-Hexyloxycarbonyloxyphenyl)-6-(2-ethylhexyl)-5,6,7,8-tetrahydroquinazoline.

EXAMPLE 4

(a) 16.7 g of 2-(4-cyanophenyl)-6-n-heptyl-5,6,7,8-tetrahydroquinazoline and a solution of 6 g of potassium hydroxide in 50 ml of ethanol are heated to the boil for 4 hours. The reaction mixture is then poured into 200 ml of water, the aqueous solution is acidified with 10% strength aqueous hydrochloric acid (pH 2-3) and the acid solution is extracted by shaking three times with 100 ml of diethyl ether. The organic phases are dried over calcium chloride and evaporated. 14 g of 2-(4-carboxyphenyl)-6-n-heptyl-5,6,7,8-tetrahydroquinazoline resin remains as a gray-white, crystalline mass.

The following are prepared analogously
2-(4-carboxyphenyl)-6-methyl-5,6,7,8-tetrahydroquinazoline,
2-(4-carboxyphenyl)-6-ethyl-5,6,7,8-tetrahydroquinazoline,
2-(4-carboxyphenyl)-6-n-propyl-5,6,7,8-tetrahydroquinazoline,
2-(4-carboxyphenyl)-6-n-butyl-5,6,7,8-tetrahydroquinazoline,
2-(4-carboxyphenyl)-6-n-pentyl-5,6,7,8-tetrahydroquinazoline,
2-(4-carboxyphenyl)-6-n-hexyl-5,6,7,8-tetrahydroquinazoline,
2-(4-carboxyphenyl)-6-n-octyl-5,6,7,8-tetrahydroquinazoline,
2-(4-carboxyphenyl)-6-n-nonyl-5,6,7,8-tetrahydroquinazoline,
2-(4-carboxyphenyl)-6-n-decyl-5,6,7,8-tetrahydroquinazoline,
2-(4-carboxyphenyl)-6-(2-methylbutyl)-5,6,7,8-tetrahydroquinazoline, and
2-(4-carboxyphenyl)-6-(2-ethylhexyl)-5,6,7,8-tetrahydroquinazoline.

(b) 7 g of 2-(4-carboxyphenyl)-6-n-heptyl-5,6,7,8-tetrahydroquinazoline together with 15 g of sulfur tetrafluoride is heated in a sealed tube to 100° for 8 hours. After cooling, excess sulfur tetrafluoride is removed by blowing in nitrogen and the remaining 2-(4-trifluoromethylphenyl)-6-n-heptyl-5,6,7,8-tetrahydroquinazoline is recrystallized from ethanol; yield 4.8 g of colorless crystals.

The following are prepared analogously:
2-(4-trifluoromethylphenyl)-6-methyl-5,6,7,8-tetrahyroquinazoline, 2-(4-trifluoromethylphenyl)-6-ethyl-5,6,7,8-tetrahydroquinazoline,
2-(4-trifluoromethylphenyl)-6-n-propyl-5,6,7,8-tetrahydroquinazoline,
2-(4-trifluoromethylphenyl)-6-n-butyl-5,6,7,8-tetrahydroquinazoline,
2-(4-trifluoromethylphenyl)-6-n-pentyl-5,6,7,8-tetrahydroquinazoline,
2-(4-trifluoromethylphenyl)-6-n-hexyl-5,6,7,8-tetrahydroquinazoline,
2-(4-trifluoromethylphenyl)-6-n-octyl-5,6,7,8-tetrahydroquinazoline,
2-(4-trifluoromethylphenyl)-6-n-nonyl-5,6,7,8-tetrahydroquinazoline,
2-(4-trifluoromethylphenyl)-6-n-decyl-5,6,7,8-tetrahydroquinazoline,
2-(4-trifluoromethylphenyl)-6-(2-methylbutyl)-5,6,7,8-tetrahydroquinazoline, and
2-(4-trifluoromethylphenyl)-6-(2-ethylhexyl)-5,6,7,8-tetrahydroquinazoline.

The following examples relate to liquid-crystalline dielectrics according to the invention.

EXAMPLE 5

A mixture of 40 parts by weight of 4-(trans-4-n-propylcyclohexyl)-benzonitrile and 60 parts by weight of 4-(trans-4-n-pentylcyclohexyl)-benzonitrile has a nematic phase in the temperature range from +8° to +51°. A ternary liquid-crystalline dielectric having a nematic phase in the temperature range from +2° to +60° is obtained by adding 22 parts by weight of 2-(4-n-butoxyphenyl)-6-n-hexyl-5,6,7,8-tetrahydroquinazoline.

EXAMPLE 6

A mixture of 35 parts by weight of 4-(trans-4-n-propylcyclohexyl)-benzonitrile and 65 parts by weight of 4-n-pentyl-4'-cyanobiphenyl has a nematic phase in the temperature range from +3° to +39°. A liquid-crystalline dielectric which represents a ternary eutectic having a nematic phase in the temperature range from −3° to +48° is obtained by adding 19 parts by weight of 2-(4-n-butoxyphenyl)-6-n-hexyl-5,6,7,8-tetrahydroquinazoline.

EXAMPLE 7

A mixture of 30 parts by weight of 4(trans-4-n-butylcyclohexyl)-benzonitrile, 55 parts by weight of 4-n-pentylphenyl anisate and 15 parts by weight of 4-(trans-4-n-pentylcyclohexyl)-4'-cyanobiphenyl has a nematic phase in the temperature range from +6° to +64° and a DCA of +8.1. A liquid-crystalline dielectric which is a quaternary eutectic with a nematic phase in the temperature range from +2° to +67° and a DCA of +9.3 is obtained by adding 12 parts by weight of 2-(4-cyanophenyl)-6-n-hexyl-5,6,7,8-tetrahydroquinazoline.

EXAMPLE 8

A mixture of 31 parts by weight of 4-(trans-4-n-propylcyclohexyl)-1-n-butoxybenzene, 33 parts by weight of 4'-n-pentylphenyl 4-n-hexyloxybenzoate and 36 parts by weight of 4'-n-heptylphenyl 4-n-hexanoyloxybenzoate has a nematic phase in the temperature range from +6° to +48°, a DCA of −0.2 and an optical anisotropy of +0.12. A liquid-crystalline dielectric with a nematic phase in the temperature range from +3° to +51°, a DCA of +2.5 and an optical anisotropy of +0.13 is obtained by adding 10 parts by weight of 2-(4-cyanophenyl)-6-n-pentyl-5,6,7,8-tetrahydroquinazoline.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A tetrahydroquinazoline of the formula

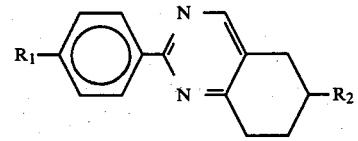

wherein $R_1$ is alkyl, alkoxy, alkanoyloxy or alkoxycarbonyloxy of up to 8 carbon atoms in each case, CN, $CF_3$, F, Cl, Br or $NO_2$; and $R_2$ is alkyl of up to 10 carbon atoms.

2. A tetrahydroquinazoline of claim 1 wherein $R_1$ is CN.

3. A tetrahydroquinazoline of claim 1, wherein $R_1$ is alkyl, alkoxy or alkanoyloxy of up to 6 carbon atoms.

4. A tetrahydroquinazoline of claim 1, wherein $R_1$ is CN, $CF_3$, F, Cl, Br or $NO_2$.

5. In a liquid-crystalline dielectric comprising a mixture of liquid-crystalline components, the improvement wherein at least one component is a tetrahydroquinazoline of claim 1.

6. A liquid-crystalline dielectric of claim 5, comprising 1 to 50 percent by weight of a tetrahydroquinazoline of the formula

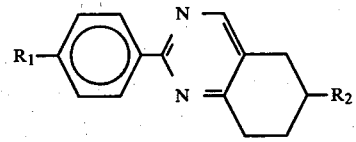

wherein $R_1$ is alkyl, alkoxy, alkanoyloxy or alkoxycarbonyloxy of up to 8 carbon atoms in each case, CN, $CF_3$, F, Cl, Br or $NO_2$; and $R_2$ is alkyl of up to 10 carbon atoms.

7. In an electro-optical display element having a liquid crystal cell which is based on a liquid-crystalline dielectric, the improvement wherein the liquid-crystalline dielectric is that of claim 5.

* * * * *